United States Patent
Plasson et al.

(10) Patent No.: US 9,894,903 B2
(45) Date of Patent: Feb. 20, 2018

(54) **METHOD FOR BIOLOGICALLY COMBATING *NAEGLERIA FOWLERI*, AND DISINFECTING AGENT CONTAINING PROTOZOA OF THE SPECIES *WILLAERTIA MAGNA***

(71) Applicant: AMOEBA, Chassieu (FR)

(72) Inventors: Fabrice Plasson, Lyons (FR); Mouh Oulhadj Mameri, Vaulx en Velin (FR)

(73) Assignee: AMOEBA, Chassieu (FR)

( * ) Notice: Subject to any disclaimer, the term of this patent is extended or adjusted under 35 U.S.C. 154(b) by 0 days.

(21) Appl. No.: 15/030,844

(22) PCT Filed: Oct. 22, 2014

(86) PCT No.: PCT/FR2014/052691
§ 371 (c)(1),
(2) Date: Apr. 20, 2016

(87) PCT Pub. No.: WO2015/059411
PCT Pub. Date: Apr. 30, 2015

(65) Prior Publication Data
US 2016/0249624 A1     Sep. 1, 2016

(30) Foreign Application Priority Data
Oct. 23, 2013    (FR) .................................... 13 60347

(51) Int. Cl.
    *A01N 63/00*     (2006.01)
    *C02F 1/50*     (2006.01)
    *C02F 3/34*     (2006.01)

(52) U.S. Cl.
    CPC ............... *A01N 63/00* (2013.01); *C02F 1/50* (2013.01); *C02F 3/34* (2013.01); *C02F 2303/04* (2013.01)

(58) Field of Classification Search
    CPC ....... A01N 63/00; C02F 1/50; C02F 2303/04; C02F 3/34
See application file for complete search history.

(56) References Cited

U.S. PATENT DOCUMENTS

| 5,344,838 | A | 9/1994 | Wachman et al. |
| 8,168,167 | B2 * | 5/2012 | Bodennec .............. A01N 63/00 424/93.1 |

FOREIGN PATENT DOCUMENTS

| FR | 2994980 | * | 3/2014 |
| WO | WO 2008/043969 | | 4/2008 |

OTHER PUBLICATIONS

International Search Report issued in International patent application No. PCT/FR2014/052691, dated Feb. 4, 2015.

* cited by examiner

*Primary Examiner* — Debbie K Ware
(74) *Attorney, Agent, or Firm* — Seyfarth Shaw LLP

(57) ABSTRACT

The invention relates to a process for combating the proliferation of the *Naegleria* genus and in particular of the species *Naegleria fowleri*, with the exception of the treatment methods applied to the human or animal body, characterized in that it uses protozoa of the species *Willaertia magna*, and also a disinfecting agent containing such protozoa.

4 Claims, 4 Drawing Sheets

Figure 1:
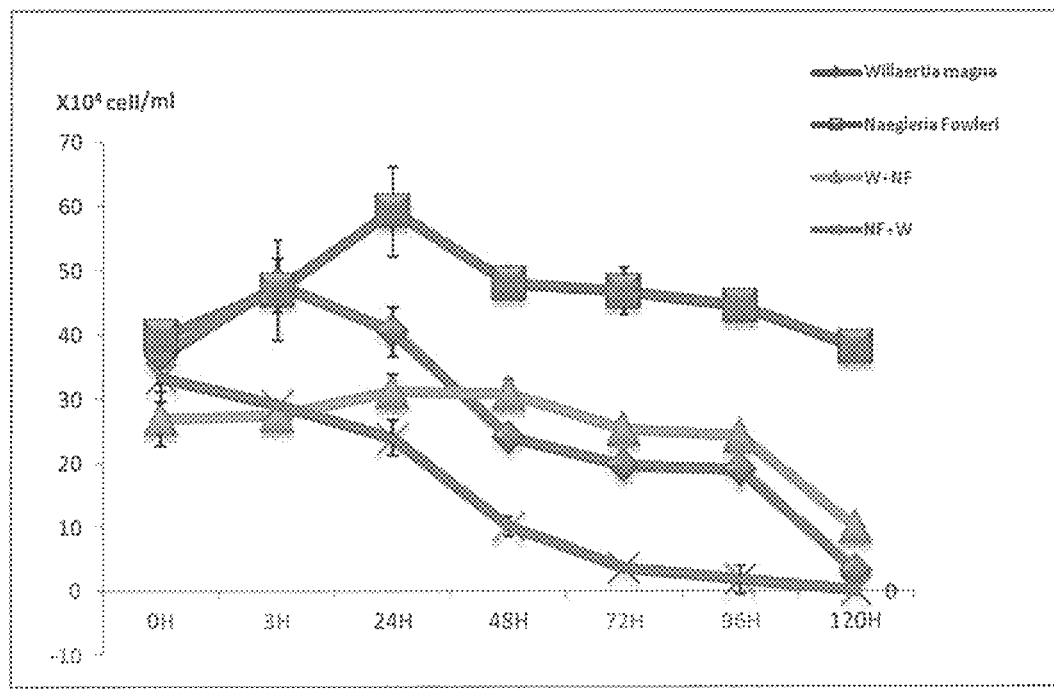

Time 0 Hour  Time 3 Hours  Time 24 Hours

Time 48 Hours  Time 72 Hours  Time 96 Hours

METHOD FOR BIOLOGICALLY COMBATING *NAEGLERIA FOWLERI*, AND DISINFECTING AGENT CONTAINING PROTOZOA OF THE SPECIES *WILLAERTIA MAGNA*

CROSS-REFERENCE TO RELATED APPLICATION

This application is a United States National Stage Application of PCT International Patent Application No. PCT/FR2014/052691, which was filed on Oct. 22, 2014, which claims priority to French Patent Application No. 1360347, which was filed Oct. 23, 2013, the disclosures of each of which is incorporated herein by reference in their entirety.

FIELD OF THE INVENTION

The present invention relates to a novel process for biologically controlling the presence of the *Naegleria* genus and in particular of the species *Naegleria fowleri*, and the proliferation thereof.

BACKGROUND OF THE INVENTION

*Naegleria fowleri* (*N.f.*) is a free-living ameba belonging to the family Vahlkampfiidae. This ameba is responsible in humans for a serious pathological condition, which is very fortunately extremely rare (235 cases detected in 2007): primary amebic meningoencephalitis (PAM) (Cervantes-Sandoval I, 2008; Kemble S K, 2012; TW, 2010; Su M Y, 2013). Infection with these free-living amebae has a catastrophic prognosis in approximately one week and a few weeks with antibiotic treatment (Su M Y, 2013). There is no truly effective treatment against this infection; very fortunately, the diseases is rare and requires the coming together of specific conditions in order to trigger PAM. These particular conditions and also the inoculum required are still unknown at the current time. However, some drugs and antibiotics appear to influence the progression of the infection, such as amphotericin B, rifampicin and miconazole which, when combined, have proved to be effective on 2 or 3 individuals. In 1992, the literature reported only 7 cases of proven survival after PAM (Gautam P L, 2012) and only in very young subjects from 2 to 14 years old and in whom the treatment and the infection left more or less significant neurological after effects. The survival rate is therefore even lower than for infection with the Ebola virus. Thus, the monitoring and control of this free-living ameba constitute an increasingly significant preoccupation.

Generally, it is known that *Naegleria fowleri* has a ubiquitous distribution in the environment (Martinez A J, 1997), since this ameba has been isolated from the soil, river water and lake water (Jamerson M, 2009) or industrial wastewater, and biofilms (Goudot S, 2012; S. A. Huws, 2005), characteristics that it shares with other free-living amebae. Several potentially pathogenic bacteria, including *Legionella pneumophila*, have developed mechanisms for surviving and replicating inside free-living amebae (Huang S W, 2010; De Jonckheere, 2011). Furthermore, it has been demonstrated that nuclear power stations greatly contribute to the development of the ameba *Naegleria fowleri* through the reheating of river water by several degrees. Indeed, the ameba *Naegleria fowleri* is thermophilic with development temperature ranges of from 25° C. to 45° C. (Visvesvara G S, 2007).

EDF, which operates more than 11 nuclear power stations in France, has quantified the risk relating to the level of *Naegleria fowleri* detected in water. In order to have a better understanding of this risk, the Department of Studies and Research and the Department of Medical Studies of EDF have calculated the risks of death from PAM when swimming, as a function of the concentration of *Naegleria fowleri* in the water. This risk can be broken down in the following way:

risk for 1 swim=probability of inhaling "n" *Naegleria fowleri* when swimming in water where *Naegleria fowleri* are present at a concentration "c" (10 ml of water inhaled per swim)

multiplied by probability of death when "n" *Naegleria fowleri* have been inhaled (modeling according to animal data).

When choosing the normal log model, which gives the lowest estimations, and which fits well with the actual data (USA, Australia, New Zealand), the following risks are obtained:

Concentration Risk for an Amount n of *N.f.* In Swimming Water

1 *Naegleria fowleri*/liter, risk=10-8, i.e. one death per 100 million swims

10 *Naegleria fowleri*/liter, risk $1.45 \times 10^{-7}$, i.e. one death per 7 million swims 100 *Naegleria fowleri*/liter, risk=$7.24 \times 10^6$, i.e. one death per 140 000 swims 1000 *Naegleria fowleri*/liter, risk=$1.34 \times 10^{-3}$, i.e. one death per 746 swims.

In accordance with the recommendations of the Conseil supérieur d'hygiène publique de France (CSHPF) [French High Council for Public Hygiene], the exceeding of the limiting value of 100 *Naegleria fowleri* (*N.f.*) per liter must result in swimming being prohibited (cf. in particular the opinion of the CSHPF of May 4, 2004, relating to the feedback from experience of the antiamebic treatments with monochloramine carried out in 2003 by EDF on the electricity-producing nuclear power stations (CNPE) of Bugey, Chooz, Dampierre, Golfech and Nogent).

BRIEF SUMMARY OF THE INVENTION

In this context, the inventors have demonstrated, totally unexpectedly, that the amebic genus *Willaertia magna* (*W.m.*) eradicates the free-living amebae *Naegleria fowleri*. This biocidal effect is backed up by the already demonstrated predation capacity of *Willaertia magna* toward other bacterial agents such as the bacteria *Legionella pneumophila, Pseudomonas* and *Listena* (Bodennec Jacques 2006).

A subject of the present invention is therefore first of all a process for controlling the proliferation of *Naegleria*, in particular *Naegleria fowleri*, which uses protozoa of the *Willaertia* genus, preferably *Willaertia magna*. The processes in accordance with the invention do not include the treatment methods applied to the human or animal body. In the process according to the invention, it is usually a gas or liquid stream which is treated with protozoa of the *Willaertia* genus, and in particular of the species *Willaertia magna*. However, it may also be a solid surface.

BRIEF DESCRIPTION OF THE INVENTION

Figure 2:
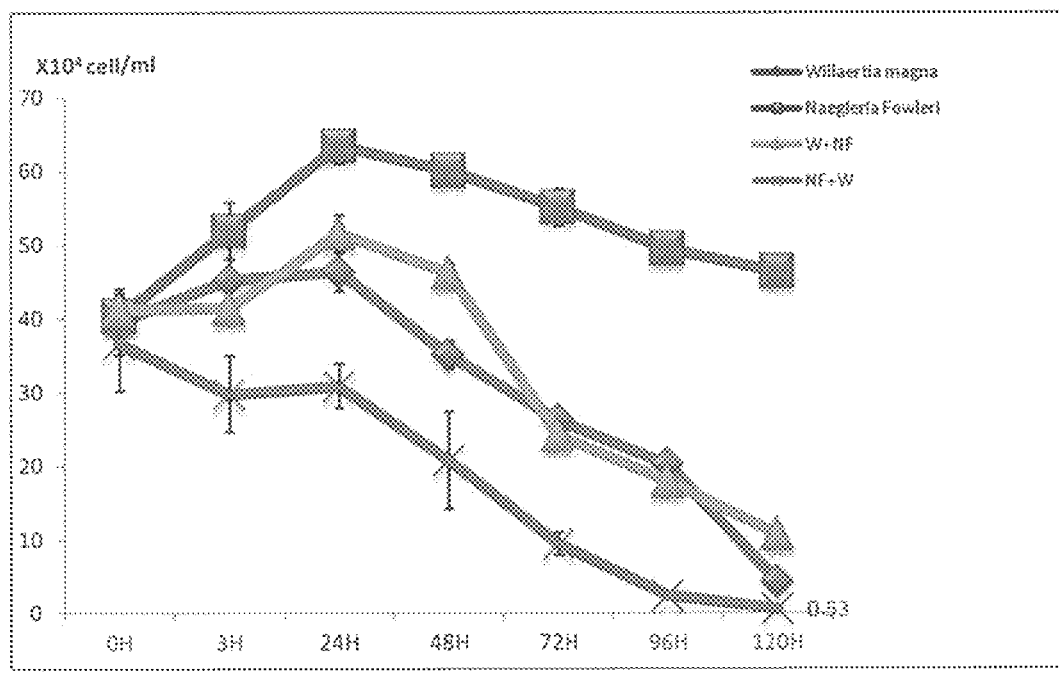
Figure 3:
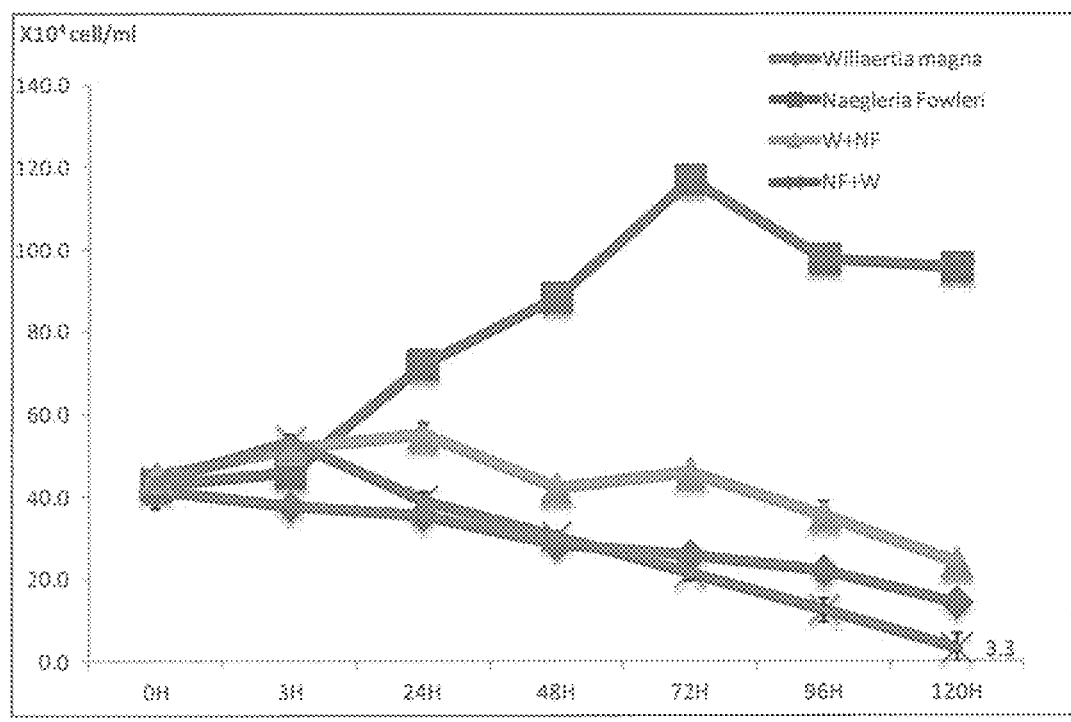

FIGS. 1, 2 and 3 show experiments of coculture (*Willaertia magna/Naegleria fowleri*) and of control monocultures of amebae. They show the spontaneous evolution of the respective populations of *Willaertia magna* and *Naegleria* fowleri amebae after coculture at an initial *Willaertia/ Naegleria* ratio of 1 compared with the evolution of the respective populations of amebae in monoculture. In FIGS. 1, 2 and 3, the curve with diamond-shaped points (♦), called *Willaertia magna*, describes the measured concentration of *Willaertia magna* alone in culture in a sterile PAS medium. The curve with square-shaped points (■), called *Naegleria fowleri*, describes the measured concentration of *Naegleria fowleri*r alone in culture in a sterile PAS medium. The curve with triangle-shaped points (Δ), called W+NF, describes the measured concentration of *Willaertia magna* in coculture with *Naegleria fowleri*r in a sterile PAS medium. The curve with cross-shaped points (X), called NF+W, describes the measured concentration of *Naegleria fowleri* in coculture with *Willaertia magna* in a sterile PAS medium. The data are expressed as concentration of whole cells per milliliter (ml), counted on Malassez cells.

Figure 4A:
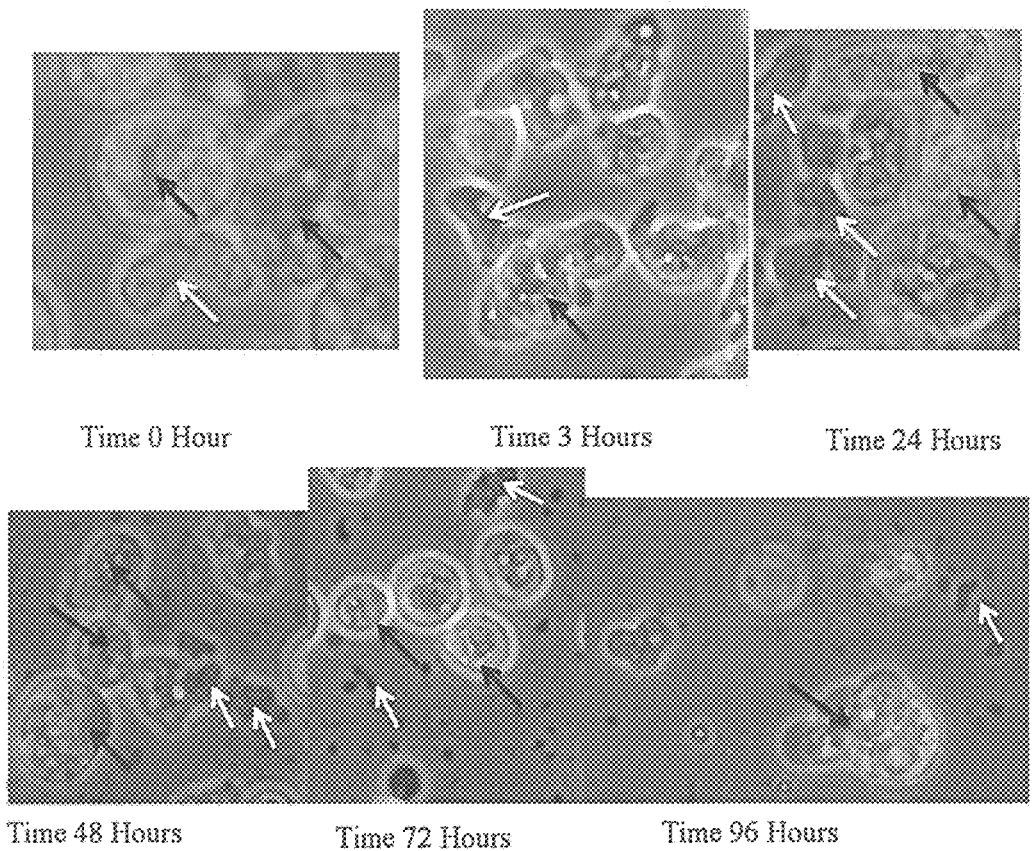
Figure 4B:
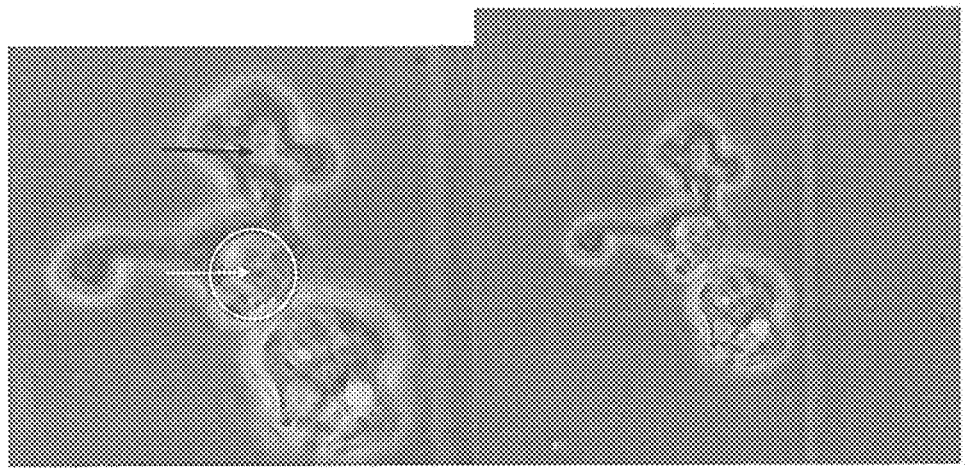

FIGS. 4a and 4b show the physiological state of the *Naegleria fowleri*r amebae over time in the presence of *Willaertia magna* amebae.

FIG. 4a corresponds to images of the rapid physiological degradation of the *Naegleria fowleri*r in cocultures with *Willaertia magna*. In FIG. 4a, the black arrows indicate the presence of *Willaertia magna* and the white arrows the presence of *Naegleria fowleri*r which are whole or in pieces.

FIG. 4b corresponds to images illustrating the phenomenon of the "kiss of death" of a *Willaertia magna* on a *Naegleria fowleri*. In FIG. 4b, the black arrow indicates the presence of *Willaertia magna* and the white arrow the presence of *Naegleria fowleri*. The white circle materializes the outlines of the *Naegleria fowleri*r cell. This "kiss of death" phenomenon has been described in the literature (Berke G. Source Department of Cell Biology, 1995) as a contact which allows granzyme to pass through, resulting in the apoptosis of the target cell.

Figure 5:
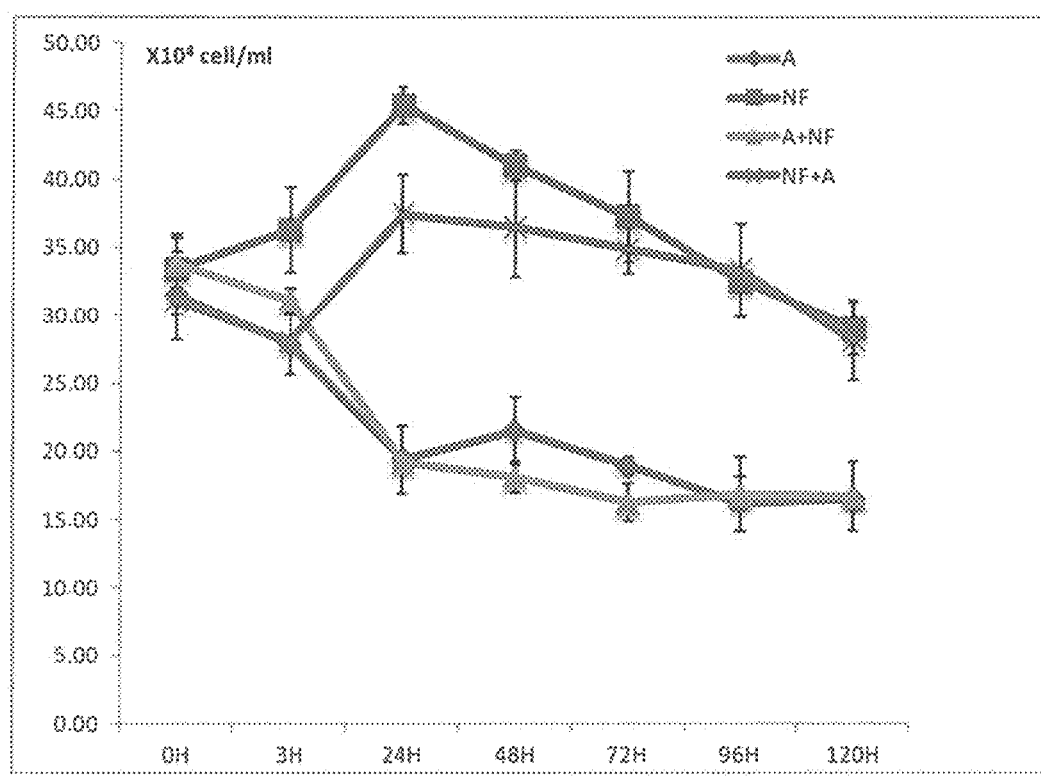

FIG. 5 shows an experiment of coculture (*Acanthamoeba castelanii/Naegleria fowleri*) and of control monocultures of amebae. In FIG. 5, curve A composed of diamond-shaped points (♦) represents a monoculture of *Acanthamoeba castellanii*. Curve A+NF composed of triangle-shaped points (Δ) represents the concentration of *Acanthamoeba castellanii* in coculture with *Naegleria fowleri*. Curve NF composed of square-shaped points (■) represents a monoculture of *Naegleria fowleri*. Curve NF+A composed of cross-shaped points (X) represents the concentration of *Naegleria fowleri* in coculture with *Acanthamoeba castellanii*.

DETAILED DESCRIPTION OF THE INVENTION

The process according to the invention is in particular of use in the disinfection of sanitation water or industrial water distribution networks, cooling circuits for example of nuclear type, of industrial plants, or air-conditioning networks. It can be implemented for controlling the formation of biofilms in water pipes, or surfaces which may or may not be in contact with human or animal foodstuffs.

The protozoa may be directly added to the water or to the liquids circulating in the pipes or in the networks to be treated. It is also possible to spray them, for example in the form of an aqueous solution as an aerosol, in the industrial networks, chimneys, plants, and on the industrial surfaces, to be disinfected.

Advantageously, the protozoa used in the context of the invention correspond to the strain deposited on Aug. 21, 2006, under number PTA 7824 at the ATCC or to the strain deposited on Aug. 21, 2006, under number PTA 7825 at the ATCC, these two strains having been deposited in the names of the CENTRE NATIONAL DE LA RECHERCHE SCIENTIFIQUE (CNRS) [French National Center for Scientific Research]-3 rue Michel Ange-75794 PARIS CEDEX 16/France and UNIVERSITE LYON 1 CLAUDE BERNARD [Lyon 1 Claude Bernard University]-43 Boulevard du 11 Nov. 1918-69622 VILLEURBANNE Cedex/France.

The protozoa belonging to the *Willaertia* genus corresponding to the strain deposited under number PTA 7824 at the ATCC or to the strain deposited under number PTA 7825 at the ATCC are an integral part of the invention. Said deposited strains are also described in the publication of the PCT international application WO 2008/043969.

Such protozoa may therefore be used in disinfecting agents, in particular intended for eliminating *Naegleria fowleri* amebae and for controlling proliferation and contamination by *Naegleria fowleri*.

Furthermore, a subject of the invention is a disinfecting agent containing protozoa of the *Willaertia* genus, and in particular of the species *Willaertia magna*. The protozoa corresponding to the strain deposited under number PTA 7824 at the ATCC or to the strain deposited under number PTA 7825 at the ATCC will be preferred. Advantageously, the disinfecting agent according to the invention is in the form of an aqueous solution or suspension, for example in distilled water. The disinfecting agent may be in a sprayable form, for example as an aerosol or any other means of application.

The *Naegleria fowleri* proliferation-inhibiting activity of the protozoa of the *Willaertia* genus, and in particular of the species *Willaertia magna*, has been demonstrated by the inventors by comparing the replication of *Naegleria fowleri* in the presence and absence of the *Willaertia* genera, and in particular of the species *Willaertia magna*. The inventors have also demonstrated the unique nature of this *Naegleria fowleri* growth inhibition by the *Willaertia magna* genus by using another species of free-living ameba, *Acanthamoeba*, as control strain which causes no *Naegleria fowleri* growth inhibition.

Given the absence of curative or prophylactic treatment of the *Naegleria fowleri* risk to humans of a mortality rate of more than 95% in less than one week, this invention is a major scientific advance for controlling this amebic plague with a neutral impact on the environment and on humans. Indeed, EC regulation No. 1271/2008 currently recognizes that the *Willaertia magna* strain is not in the dangerous class of category and does not mention any danger or recommendation for caution, unlike the monochloramine currently used.

Furthermore, the present invention is directed toward the use of the disinfecting agent according to the invention and/or the protozoa of the *Willaertia* genus, and in particular of the species *Willaertia magna*, and the protozoa corresponding to the strain deposited under number PTA 7824 at the ATCC or to the strain deposited under number PTA 7825 at the ATCC, as biocide on *Naegleria*.

The examples hereinafter make it possible to illustrate the invention but are in no way limiting in nature.

1. Materials and Methods
  1.1. Strains Used:
  Amebae: the strains used belong to three different amebic species:
    *Naegleria fowleri* (ATCC 30809)
    *Acanthamoeba castellanii* (ATCC 30010)
    *Willaertia magna* (strains deposited at the ATCC under Nos PTA 7824 and PTA 7825).

These three strains are cultured axenically, in the presence of 10% of fetal calf serum, on SCGYEM medium (Serum Casein Glucose Yeast Extract Medium), distributed into GREINER™ tubes in a proportion of 3 ml per tube. In maintenance, the vegetative forms are subcultured every 8-9 days. For the cocultures, 3-to-4-day subcultures are used so as to have trophozoites right in the exponential growth phase.

The SCGYEM medium is obtained as follows:

| | |
|---|---|
| Casein (MERCK, 1.02244.010) | 10 g |
| $Na_2HPO_4$ | 1.325 g |
| $KH_2PO_4$ | 0.8 g |
| Glucose | 2.5 g |
| Yeast extract (DIFCO 0127-17-9) | 5 g |
| Distilled water | 900 ml |
| Fetal calf serum | 100 ml |

2.5 ml of NaOH (1N), and then $Na_2HPO_4$ and $KH_2PO_4$, are added to the 900 ml of distilled water. After having slightly heated on a hot plate, the casein is gradually added with magnetic stirring. After the casein has dissolved, the glucose and the yeast extract are incorporated.

After complete dissolution, the medium is filtered successively on glass fiber (SARTORIUS SM 6513400), and then on a 1 µm membrane (WHATMAN 7190 004). The medium is than aliquoted into glass bottles. The bottles are sterilized in an autoclave for 20 minutes at 120° C. Before the definitive use and distribution of the medium, the fetal calf serum is added sterily, under a laminar flow hood, in a proportion of 10% of the final volume.

1.2. Preparation of the *Willaertia magna* and *Naegleria fowleri* Amebic Stock Suspensions:

The preparation of each initial amebic suspension (stock suspension) is carried out using 4 flasks (T 175 ml) of axenic culture of each ameba cultured in SCGYEM medium. These stock amebic suspensions of *Naegleria fowleri, Acanthamoeba* and *Willaertia magna* are harvested at the end of the exponential growth phase, which is generally obtained 4 to 5 days after beginning the culture.

In order to increase the amebic concentration harvested, the flasks are passed through an ice bath for 5 to 10 minutes, and then stirred manually in order to collect as many amebae as possible.

The content of these 4 flasks is combined in order to count the amebic suspension obtained on a THOMA cell ([C]/ml).

The amebic suspensions are transferred into a 50 ml tube of FALCON® type in order to remove the SCGYEM culture medium by centrifugation at 1500 g for 10 minutes. The amebic pellets resulting from the first centrifugation are rinsed twice by washing with sterile distilled water and centrifuged at 1500 g for 10 minutes. At the end of the 2 washes, the final pellet is taken up in a volume of sterile water of 40 ml.

1.3. Demonstration of the Biocidal Effect of *Willaertia magna* on *Naegleria fowleri* (Strain ATCC 30809):

The amebic cocultures are carried out in T 25 ml flasks containing 10 ml of sterile PAS (Page's Amoeba Saline) medium. The flasks of amebic coculture are inoculated in a proportion of $1\times10^5$ *Willaertia magna*/ml and $1\times10^5$ *Naegleria fowleri*/ml from the axenic amebic suspensions previously counted on a Malassez hemocytometer. The infestation of the *Willaertia magna* by *Naegleria fowleri* is carried out by fixing a *Naegleria fowleri/Willaertia magna* ratio of 1. The T 25 ml flasks are incubated in an incubator at 30° C.

The PAS medium is obtained as follows:

| Solution 1: | Amount for 500 ml of $H_2O$ | Supplier | [M] |
|---|---|---|---|
| NaCl (Molecular weight: 58.44) | 12.0 g | Fisher S271-3 | 0.41 |
| $MgSO_4 \cdot 7H_2O$ (Molecular weight heptahydrate: 246.47) | 0.40 g | Sigma 63138 (heptahydrate) | 0.0032 |
| $CaCl_2 \cdot 6H_2O$ (Molecular weight: 219.08) | 0.60 g | Sigma 442909-1 kg | 0.0055 |

| Solution 2: | | | |
|---|---|---|---|
| $Na_2HPO_4$ (Anhydrous molecular weight: 141.96) | 14.20 g | Fluka 71629-100 g | 0.2 |
| $KH_2PO_4$ (Anhydrous molecular weight: 136.09) | 13.60 g | Sigma P5655 | 0.2 |

Sterily filter solutions 1 and 2 using a 0.22 µm filter. In order to obtain 1 liter of PAS medium: add 5.0 ml of solution 1 and 5.0 ml of solution 2, then adjust the volume to 1 liter with sterile distilled water.

The *Willaertia magna* and *Naegleria fowleri* control amebic monocultures are cultured separately in T 25 ml flasks in 10 ml of sterile PAS medium.

The flasks are inoculated in a proportion of $1\times10^5$ *Willaertia magna*/ml for the *Willaertia magna* control and $1\times10^5$ *Naegleria fowleri*/ml for the *Naegleria fowleri* control, from the axenic amebic suspensions previously counted on a Malassez hemocytometer. The control T 25 ml flasks are incubated in an incubator at 30° C.

Each condition is carried out in triplet. Each count on a Malassez cell is repeated 5 times. The experiment was repeated three (3) times over a period of 3 months.

The fates of the *Naegleria fowleri* and *Willaertia magna* amebae in coculture and in the control flasks are determined in the following way:

The amebic concentrations are monitored for 120 hours after infestation by *Naegleria fowleri*. At each time interval (at 3 hours and then every 24 hours), the coculture and control flasks are sampled and examined both from the point of view of the cell growth of the two amebae and from the point of view of their morphological and dynamic state. For each flask examined:

The amebae are counted directly on a Malassez cell.
At 120 hours, the low level of *Naegleria fowleri* amebae no longer allows reliable counting on a Malassez cell, hence the joint use of the MPN (Most Probable Number) method. This method which is widely used for counting amebae, has the advantage of being more accurate, but also of distinguishing amebae which are whole and living from amebae which are whole but dead.

2. Results

FIGS. 1, 2 and 3 show experiments of coculture (*Willaertia magna/Naegleria fowleri*) and of control monocultures of amebae.

They show the spontaneous evolution of the respective populations of *Willaertia magna* and *Naegleria fowleri* amebae after coculture at an initial *Willaertia/Naegleria* ratio of 1 compared with the evolution of the respective populations of amebae in monoculture.

FIGS. 4a and 4b show the physiological state of the *Naegleria fowleri* amebae over time in the presence of *Willaertia magna* amebae. FIG. 4a corresponds to images of the rapid physiological degradation of the *Naegleria fowleri* in cocultures with *Willaertia magna*. FIG. 4b corresponds to images illustrating the phenomenon of the "kiss of death" of a *Willaertia magna* on a *Naegleria fowleri*.

FIG. 5 shows an experiment of coculture (*Acanthamoeba castelanii/Naegleria fowleri*) and of control monocultures of amebae.

In FIGS. 1, 2 and 3, the curve with diamond-shaped points (♦), called *Willaertia magna*, describes the measured concentration of *Willaertia magna* alone in culture in a sterile PAS medium.

The curve with square-shaped points (■), called *Naegleria fowleri*, describes the measured concentration of *Naegleria fowleri* alone in culture in a sterile PAS medium.

The curve with triangle-shaped points (Δ), called W+NF, describes the measured concentration of *Willaertia magna* in coculture with *Naegleria fowleri* in a sterile PAS medium.

The curve with cross-shaped points (X), called NF+W, describes the measured concentration of *Naegleria fowleri* in coculture with *Willaertia magna* in a sterile PAS medium.

The data are expressed as concentration of whole cells per milliliter (ml), counted on Malassez cells.

In FIG. 4a, the black arrows indicate the presence of *Willaertia magna* and the white arrows the presence of *Naegleria fowleri* which are whole or in pieces.

In FIG. 4b, the black arrow indicates the presence of *Willaertia magna* and the white arrow the presence of *Naegleria fowleri*. The white circle materializes the outlines of the *Naegleria fowleri* cell. This "kiss of death" phenomenon has been described in the literature (Berke G. Source Department of Cell Biology, 1995) as a contact which allows granzyme to pass through, resulting in the apoptosis of the target cell.

In FIG. 5, curve A composed of diamond-shaped points (♦) represents a monoculture of *Acanthamoeba castellanii*.

Curve A+NF composed of triangle-shaped points (Δ) represents the concentration of *Acanthamoeba castellanii* in coculture with *Naegleria fowleri*.

Curve NF composed of square-shaped points (■) represents a monoculture of *Naegleria fowleri*.

Curve NF+A composed of cross-shaped points (X) represents the concentration of *Naegleria fowleri* in coculture with *Acanthamoeba castellanii*.

2.1. *Willaertia manga* Totally Inhibits the Growth of *Naegleria fowleri*

As indicated by the cross-shaped curves of FIGS. 1, 2 and 3 representing the evolution of *Naegleria fowleri* in coculture with *Willaertia magna*, a detachment very rapidly takes place, at around 24 hours, in the *Naegleria fowleri* population curve. This decrease in the *Naegleria fowleri* population is observed only in the presence of *Willaertia magna*. The control curves (curves with square-shaped points) of *Naegleria fowleri* in monoculture in experiments 1, 2 and 3 (FIGS. 1, 2 and 3) at 24 hours are all undergoing growth. Moreover, the level of *Naegleria fowleri* in monoculture virtually doubles at 24 hours.

It is notable that microscopic observation confirms a crucial morphological change in the *Naegleria fowleri* in coculture with *Willaertia magna* as early as 24 hours (FIG. 4). The physiological condition of the *Naegleria fowleri* cell changes from a spread out trophozoite form to a stressed form which is more round, but not yet similar to the cyst form. The inside of the *Naegleria fowleri* cell becomes opaque, masking the internal vacuoles, a sign of growth of the amebae. The size of the *Naegleria fowleri* cells in the presence of *Willaertia magna* is less than half that in monoculture as early as 3 hours of coculture (FIG. 4a). The mode of predation of the *Willaertia magna* amebae is based on phagocytosis. FIG. 4b demonstrates, in the first 24 hours, a phenomenon of inhibition similar to the "kiss of death". The phagocytosis of *Naegleria fowleri* by *Willaertia magna* indeed occurs, but only after 25 hours of coculture corroborated by the presence of *Willaertia magna* containing *Naegleria fowleri* in these phagosomes (data not reported).

All of the experiments carried out demonstrate a maximum inhibition effect with complete elimination of *Naegleria fowleri* in 120 hours. The reading in a Malassez cell at 120 hours counts the *Naegleria fowleri* cells which are present and whole, but it is not possible to distinguish, using this counting, the dead cells from the living cells. Double reading on NNA agar+*E. coli* makes it possible to count the living *Naegleria fowleri* cells only derived from trophozoite forms and/or from cyst forms.

The table below indicates the concentration of amebae (*Naegleria fowleri*) obtained by reading on Malassez cells and those obtained using the MPN method. An aliquot of each flask from experiments 1, 2 and 3 (cf. FIGS. 1 to 3) of *Willaertia magna/Naegleria fowleri* coculture taken at 120 hours post-infection is inoculated onto NNA agars covered with a layer of *E. coli*.

The determination of the concentration of each species is measured by counting the number of fronts pinpointed per dish, and indicated in the MPN table in order to deduce therefrom the amebic concentration.

Nf=*Naegleria fowleri*
W.m=*Willaertia magna*

| | Measurement at 120 hours using the MPN method (limit of quantification = 4 Nf/l) | Measurement at 120 hours by counting on a Malassez cell (limit of quantification = $0.2 \times 10^4$ Nf/l) |
|---|---|---|
| Experiment 1 coculture Nf and W.m (FIG. 1) | <201 Nf/l | $0 \times 10^4$ Nf/ml |
| Experiment 2 coculture Nf and W.m (FIG. 2) | <201 Nf/l | $0.53 \times 10^4$ Nf/ml |
| Experiment 3 coculture Nf and W.m (FIG. 3) | <201 Nf/l | $3.3 \times 10^4$ Nf/ml |

This table confirms the absence of *Naegleria fowleri* fronts on the NNA agars, indicating the absence of *Naegleria fowleri* in cyst or trophozoite form living at 120 hours.

The inventors have demonstrated that the unexpected nature of a biocidal effect of *Willaertia magna* on the *Naegleria* genus and more particularly on the species *Naegleria fowleri* is not shared by other amebic species.

As indicated by FIG. 5, a coculture of the amebic genera *Acanthamoeba castellanii* and *Naegleria fowleri* does not cause any effect on the respective concentration of the two species compared with the concentration of these species that is measured in monoculture. This figure shows the absence of reciprocal action of another amebic genus, of *Acanthamoeba* type, on the evolution of the population of *Naegleria fowlerir* during coculture of these two amebae.

*Willaertia magna* is quite alone in possessing this characteristic of inhibiting the growth of *Naegleria* amebae and more particularly the species *Naegleria fowler.*

LITERATURE

Bodennec Jacques, Pernin Pierre, Dey Rafick. Novel method for biologically combating the proliferation of *Legionella pneumophila*, and novel disinfecting agent containing amoebic protozoa of the *Willaertia* genus. France Brevet 2906968. 12 Oct. 2006.

Cervantes-Sandoval I, Serrano-Luna J, Garcia-Latorre E, Tsutsumi V, Shibayama M. "Characterization of brain inflammation during primary amoebic meningoencephalitis." *Parasitol Int,* 57 (2008): 307 e13.

De Jonckheere. "Origin and evolution of the worldwide distributed pathogenic amoeboflagellate *Naegleria fowleri.*" *Infect Genet Evol.* 11, n° (7) (October; 2011): 1520-8.

Gautam P L, Sharma S, Purl S, Kumar R, Midha V, Bansal R. "A rare case of survival from primary amebic meningoencephalitis." *Indian J Crit Care Med.* 16, n° (1) (January 2012): 34-6.

Goudot S, Herbelin P, Mathieu L, Soreau S, Banas S, Jorand F. "Growth dynamic of *Naegleria fowleri* in a microbial freshwater biofilm." *Water res.* 46, n° (13) (September 2012): 3958-66.

Huang S W, Hsu B M. "Survey of *Naegleria* and its resisting bacteria-*Legionella* in hot spring water of Taiwan using molecular method." *Parasitol Res.* 106, n° (6) (May 2010): 1395-402.

Jamerson M, Remmers K, Cabral G, Marciano-Cabral F. "Survey for the presence of *Naegleria fowleri* amebae in lake water used to cool reactors at a nuclear power generating plant." *Parasitol Res.* 104, n° (5) (April; 2009): 969-78.

Kemble S K, Lynfield R, DeVries A S et al. "Fatal *Naegleria fowleri* infection acquired in Minnesota: possible expanded range of a deadly thermophilic organism." *Clin Infect Dis* 54 (2012): 805-809.

Martinez A J, Visvesvara G S. "Free-living, amphizoic and opportunistic amebas." *Brain Pathol.* 7, n° (1) (January; 1997): 583-98. Review.

S. A. Huws, A. J. McBain and P. Gilbert. "Protozoan grazing and its impact upon population dynamics in biofilm communities." *Journal of Applied Microbiology* 2005, 98, 238-244 98 (2005): 238-244.

Su M Y, Lee Shyu L Y, Lin W C, Hsiao P C, Wang C P, Ji D D, Chen K M, Lai S C. "A fatal case of *Naegleria fowleri* menigoencephalitis in Taiwan." *Korean J parasitol.* 51, n° (2) (April 2013): 203-206.

T W, Heggie. "Swimming with death: *Naegleria fowleri* infections in recreational waters." *Travel Med Infect Dis* 8 (2010): 201-206.

Visvesvara G S, Moura H, Schuster F L. "Pathogenic and opportunistic free-living amoebae: *Acanthamoeba* spp., *Balamuthia mandrillaris, Naegleria fowleri,* and *Sappinia diploidea.*" *FEMS Immunol Med Microbiol* 50 (2007): 1-26.

The invention claimed is:

1. A process for controlling the proliferation of an organism of the *Naegleria* genus, comprising contacting the organism with a protozoa of the *Willaertia magna* species corresponding to the strain deposited under number PTA 7824 at the ATCC or to the strain deposited under number PTA 7825 at the ATCC.

2. The process as claimed in claim 1, wherein a gas or liquid stream, or a solid surface, is treated with said protozoa of the *Willaertia magna* species.

3. The process as claimed in claim 1, wherein the process is implemented for the disinfection of sanitation water or industrial water distribution networks, cooling circuits of industrial or nuclear plants, or air-conditioning networks or industrial surfaces.

4. The process as claimed in claim 1, wherein the process is implemented for controlling the formation of biofilms in water pipes, or surfaces which may or may not be in contact with human or animal foodstuffs.

* * * * *